US00PP32199P2

(12) United States Plant Patent
Holtmaat

(10) Patent No.: US PP32,199 P2
(45) Date of Patent: Sep. 15, 2020

(54) ***ANEMONE* PLANT NAMED 'ANEM078'**

(50) Latin Name: ***Anemone multifida* x *Anemone sylvestris***
Varietal Denomination: ANEM078

(71) Applicant: Henricus Maria Joseph Holtmaat, Zuidwolde (NL)

(72) Inventor: Henricus Maria Joseph Holtmaat, Zuidwolde (NL)

(73) Assignee: Nova Perenne B.V., Zuidwolde (NL)

( * ) Notice: Subject to any disclaimer, the term of this patent is extended or adjusted under 35 U.S.C. 154(b) by 0 days.

(21) Appl. No.: 16/501,897

(22) Filed: Jul. 1, 2019

(51) Int. Cl.
*A01H 5/02* (2018.01)
*A01H 6/72* (2018.01)

(52) U.S. Cl.
USPC ..... Plt./263.1
CPC ..... *A01H 6/72* (2018.05)

(58) Field of Classification Search
USPC ..... Plt./263.1
CPC ..... A01H 6/72
See application file for complete search history.

(56) References Cited

PUBLICATIONS

UPOV hit on *Anemone* plant named, 'ANEM078', QZ PBR 20190349, filed Jan. 31, 2019.*

* cited by examiner

*Primary Examiner* — Anne Marie Grunberg
(74) *Attorney, Agent, or Firm* — C. A. Whealy

(57) ABSTRACT

A new and distinct cultivar of *Anemone* plant named 'ANEM078', characterized by its upright plant habit; moderately vigorous to vigorous growth habit; freely flowering habit; relatively large single-type flowers that are light yellow green to white in color; and good garden performance.

2 Drawing Sheets

Botanical designation: *Anemone multifida* x *Anemone sylvestris.*
Cultivar denomination: 'ANEM078'.

CROSS-REFERENCED TO CLOSELY RELATED APPLICATIONS

Title: *Anemone* Plant Named 'ANEM079'
Applicant: Henricus Maria Joseph Holtmaat
Filed: Concurrently with this application having application Ser. No. 16/501,900

BACKGROUND OF THE INVENTION

The present invention relates to a new and distinct cultivar of *Anemone*, botanically known as *Anemone multifida* x *Anemone sylvestris* and hereinafter referred to by the name 'ANEM078'.

The new *Anemone* plant is a product of a planned breeding program conducted by the Inventor in Zuidwolde, The Netherlands. The objective of the breeding program is to create new freely-flowering *Anemone* plants with large attractive flowers.

The new *Anemone* plant originated from a cross-pollination made by the Inventor In April, 2016 in Zuidwolde, The Netherlands of *Anemone multifida* 'Rosea', not patented, as the female, or seed, parent with an unnamed selection of *Anemone sylvestris*, not patented, as the male, or pollen, parent. The new *Anemone* plant was discovered and selected by the Inventor as a single flowering plant within the progeny of the stated cross-pollination in a controlled greenhouse environment in Zuidwolde, The Netherlands in April, 2018.

Asexual reproduction of the new *Anemone* by in vitro meristem culture in a controlled environment in Zuidwolde, The Netherlands since November, 2018 has shown that the unique features of this new *Anemone* plant are stable and reproduced true to type in successive generations.

SUMMARY OF THE INVENTION

Plants of the new *Anemone* have not been observed under all possible combinations of environmental conditions and various cultural practices. The phenotype may vary somewhat with variations in environmental conditions such as temperature and light intensity without, however, any variance in genotype.

The following traits have been repeatedly observed and are determined to be the unique characteristics of 'ANEM078'. These characteristics in combination distinguish 'ANEM078' as a new and distinct *Anemone* plant:

1. Upright plant habit.
2. Moderately vigorous to vigorous growth habit.
3. Freely flowering habit.
4. Relatively large single-type flowers that are light yellow green to white in color.
5. Good garden performance.

Plants of the new *Anemone* can be compared to plants of the female parent, 'Rosea'. Plants of the new *Anemone* differ primarily from plants of 'Rosea' in the following characteristics:

1. Plants of the new *Anemone* are taller than plants of 'Rosea'.
2. Leaves of plants of the new *Anemone* are longer than leaves of plants of 'Rosea'.

3. Plants of the new *Anemone* have light yellow green to white-colored flowers whereas plants of 'Rosea' have pink-colored flowers.

Plants of the new *Anemone* can be compared to plants of the male parent selection. Plants of the new *Anemone* differ primarily from plants of the male parent selection in the following characteristics:

1. Plants of the new *Anemone* are taller than plants of the male parent selection.
2. Leaves of plants of the new *Anemone* are shorter than leaves of plants of the male parent selection.
3. Plants of the new *Anemone* have light yellow green to white-colored flowers whereas plants of the male parent selection have pure white-colored flowers.

Plants of the new *Anemone* can be compared to plants of *Anemone multifida* 'Annabella White', not patented. In side-by-side comparisons, plants of the new *Anemone* and 'Annabella White' differ primarily in the following characteristics:

1. Plants of the new *Anemone* have longer stems than plants of 'Annabella White'.
2. Plants of the new *Anemone* have larger flowers than plants of 'Annabella White'.

Plants of the new *Anemone* can be compared to plants of *Anemone multifida* x *Anemone sylvestris* 'ANEM079', disclosed in a U.S. Plant Patent application filed concurrently having application Ser. No. 16/501,900. In side-by-side comparisons, plants of the new *Anemone* and 'ANEM079' differ primarily in flower color as plants of the new *Anemone* have light yellow green to white-colored flowers whereas plants of 'ANEM079' have purple-colored flowers. In addition, plants of the new *Anemone* are larger and are more freely branching and flowering than plants of 'ANEM079'.

BRIEF DESCRIPTION OF THE PHOTOGRAPHS

The accompanying colored photographs illustrate the overall appearance of the new *Anemone* plant showing the colors as true as it is reasonably possible to obtain in colored reproductions of this type. Colors in the photographs may differ slightly from the color values cited in the detailed botanical description which accurately describe the colors of the new *Anemone* plant.

The photograph on the first sheet is a side perspective view of a typical plant of 'ANEM078' grown in a container.

The photograph at the top of the second sheet comprises a close-up view of typical flowers of 'ANEM078'.

The photograph at the bottom of the second sheet comprises a close-up view of a typical leaf of 'ANEM078'.

DETAILED BOTANICAL DESCRIPTION

The aforementioned photographs and following observations, measurements and values describe plants grown during the spring in 17-cm containers in an outdoor nursery in Zuidwolde, The Netherlands and under cultural practices typical of commercial *Anemone* production. During the production of the plants, day temperatures ranged from 18° C. to 30° C. and night temperatures ranged from 6° C. to 18° C. Plants were eight months old when the photographs and description were taken. In the following description, color references are made to The Royal Horticultural Society Colour Chart, 2015 Edition, except where general terms of ordinary dictionary significance are used.

Botanical classification: *Anemone multifida* x *Anemone sylvestris* 'ANEM078'.

Parentage:

*Female, or seed, parent.*—*Anemone multifida* 'Rosea', not patented.

*Male, or pollen, parent.*—Unnamed selection of *Anemone sylvestris*, not patented.

Propagation:

*Type.*—In vitro meristem culture.

*Time to initiate roots, summer.*—About 20 days at temperatures about 25° C.

*Time to initiate roots, winter.*—About 25 days at temperatures about 10° C.

*Time to produce a rooted young plant, summer.*—About seven weeks at temperatures about 20° C.

*Time to produce a rooted young plant, winter.*—About nine weeks at temperatures about 18° C.

*Root description.*—Medium in thickness, fleshy; close to N199C to N199D in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Herbaceous perennial; upright habit with leaves developing from basal rosettes; numerous basal rosettes developing per plant; oblong in overall shape; moderately vigorous to vigorous growth habit; moderate growth rate.

*Plant height, soil level to top of foliar plane.*—About 45.5 cm.

*Plant height, soil level to top of floral plane.*—About 60.3 cm.

*Plant diameter.*—About 44 cm.

Branch description:

*Number of primary branches per plant.*—About 40.

*Number of secondary branches per plant.*—About 80.

*Length, primary branches.*—About 16.7 cm.

*Diameter, primary branches.*—About 3.5 mm.

*Internode length, primary branches.*—About 9.9 cm.

*Strength.*—Strong.

*Aspect.*—Mostly upright.

*Texture and luster.*—Densely pubescent; moderately glossy.

*Color, developing.*—Close to 144B; distally, tinged with close to N200C.

*Color, developed.*—Close to 144A.

Leaf description:

*Arrangement, basal leaves.*—Alternate; simple.

*Arrangement, cauline leaves.*—Whorled or opposite; simple.

*Length, basal leaves.*—About 8.7 cm.

*Width, basal leaves.*—About 10.4 cm.

*Length, cauline leaves.*—About 4.6 cm.

*Width, cauline leaves.*—About 5.3 cm.

*Shape, basal leaves.*—Roughly orbicular in outline; palmately cleft.

*Shape, cauline leaves.*—Roughly reniform in outline; palmately cleft.

*Apex, basal and cauline leaves.*—Acute.

*Base, basal leaves.*—Hastate.

*Base, cauline leaves.*—Attenuate.

*Margin, basal leaves.*—Laciniate with incised to serrate margins; depth of sinuses are deep and divergent.

*Margin, cauline leaves.*—Laciniate with serrate margins; depth of sinuses are deep and divergent.

*Texture and luster, basal and cauline leaves, upper surface*.—Sparsely pubescent, not rugose; slightly glossy.

*Texture and luster, basal and cauline leaves, lower surface*.—Moderately to densely pubescent, not rugose; very slightly glossy.

*Venation pattern, basal and cauline leaves*.—Laciniate.

*Color, basal leaves*.—Developing leaves, upper surface: Close to 143A. Developing leaves, lower surface: Close to 147B. Fully expanded leaves, upper surface: Close to 143A; venation, close to 144B. Fully expanded leaves, lower surface: Close to 146B; venation, close to 144B.

*Color, cauline leaves*.—Developing leaves, upper surface: Close to 143A. Developing leaves, lower surface: Close to 147B. Fully expanded leaves, upper surface: Close to between NN137A and 139A; venation, close to 144B. Fully expanded leaves, lower surface: Close to 147B; venation, close to 144B.

*Leaf petioles*.—Length, basal leaves: About 25.8 cm. Diameter, basal leaves: About 2 mm. Length, cauline leaves: About 2 cm. Diameter, cauline leaves: About 1.5 mm to 2 mm. Strength, basal and cauline leaves: Strong. Texture and luster, basal and cauline leaves, upper and lower surfaces: Moderately to densely pubescent; slightly glossy. Color, basal and cauline leaves, upper surface: Close to 144B. Color, basal and cauline leaves, lower surface: Close to 144A.

Flower description:

*Flower arrangement and flowering habit*.—Solitary single-type rotate flowers; freely flowering habit with 120 flowers developing per plant; flowers face mostly upright.

*Fragrance*.—None detected.

*Natural flowering season*.—Plants of the new *Anemone* begin flowering about ten weeks after planting and flower from early spring to the late spring in The Netherlands.

*Flower longevity*.—Individual flowers last about ten days on the plant; flowers not persistent.

*Flower diameter*.—About 4.1 cm.

*Flower length* (*depth*).—About 1 cm.

*Flower buds*.—Length: About 1 cm. Diameter: About 8 mm. Shape: Ovate. Texture and luster: Densely pubescent; matte. Color: Close to N200C tinged with close to 186C; marginal stripes, close to 150D.

*Petals*.—Absent.

*Sepals*.—Quantity and arrangement: About five arranged in a single whorl. Length: About 2.4 cm. Width: About 1.2 cm to 1.3 cm. Shape: Ovate to elliptic; slightly concave. Apex: Broadly and bluntly acute. Base: Cuneate. Margin: Entire. Texture and luster, upper surface: Smooth, glabrous; moderately velvety; matte. Texture and luster, lower surface: Densely pubescent; slightly glossy. Color: When opening, upper surface: Close to 150D. When opening, lower surface: Close to N200C tinged with close to 186C; towards the margins, close to 150D. Fully opened, upper surface: Close to between 150D and 155A; towards the base, tinged with close to N77D; venation, close to N77D; color does not change with development. Fully opened, lower surface: Close to 150D strongly tinged with close to N77C; venation, close to 79D; color does not change with development.

*Peduncles*.—Length: About 12 cm to 33 cm. Diameter: About 2 mm. Aspect: Mostly upright. Strength: Strong. Texture and luster: Densely pubescent; slightly glossy. Color: Close to 143A; distally, tinged with close to N200C.

*Reproductive organs*.—Androecium: Stamen number per flower: About 100. Filament length: About 4 mm. Filament color: Close to 157C. Anther shape: Oblong. Anther length: About 1 mm. Anther diameter: About 0.5 mm. Anther color: Close to 151A to 151B. Amount of pollen: Scarce. Pollen color: Close to 21B. Gynoecium: Pistil number per flower: About 175. Pistil length: About 1 mm. Stigma shape: Club-shaped. Stigma length: About 0.5 mm. Stigma diameter: About 0.5 mm. Stigma color: Close to 154D. Style length: About 0.5 mm. Style color: Close to 154D. Ovary color: Close to 144C.

*Seeds and fruits*.—To date, seed and fruit development have not been observed on plants of the new *Anemone*.

Garden performance: Plants of the new *Anemone* have been observed to have good garden performance, to tolerate high temperatures of about 35° C. and to be suitable for USDA Hardiness Zones 4 through 9.

Pathogen & pest resistance: To date, plants of the new *Anemone* have not been observed to be resistant to pathogens and pests common to *Anemone* plants.

It is claimed:

1. A new and distinct *Anemone* plant named 'ANEM078' as illustrated and described.

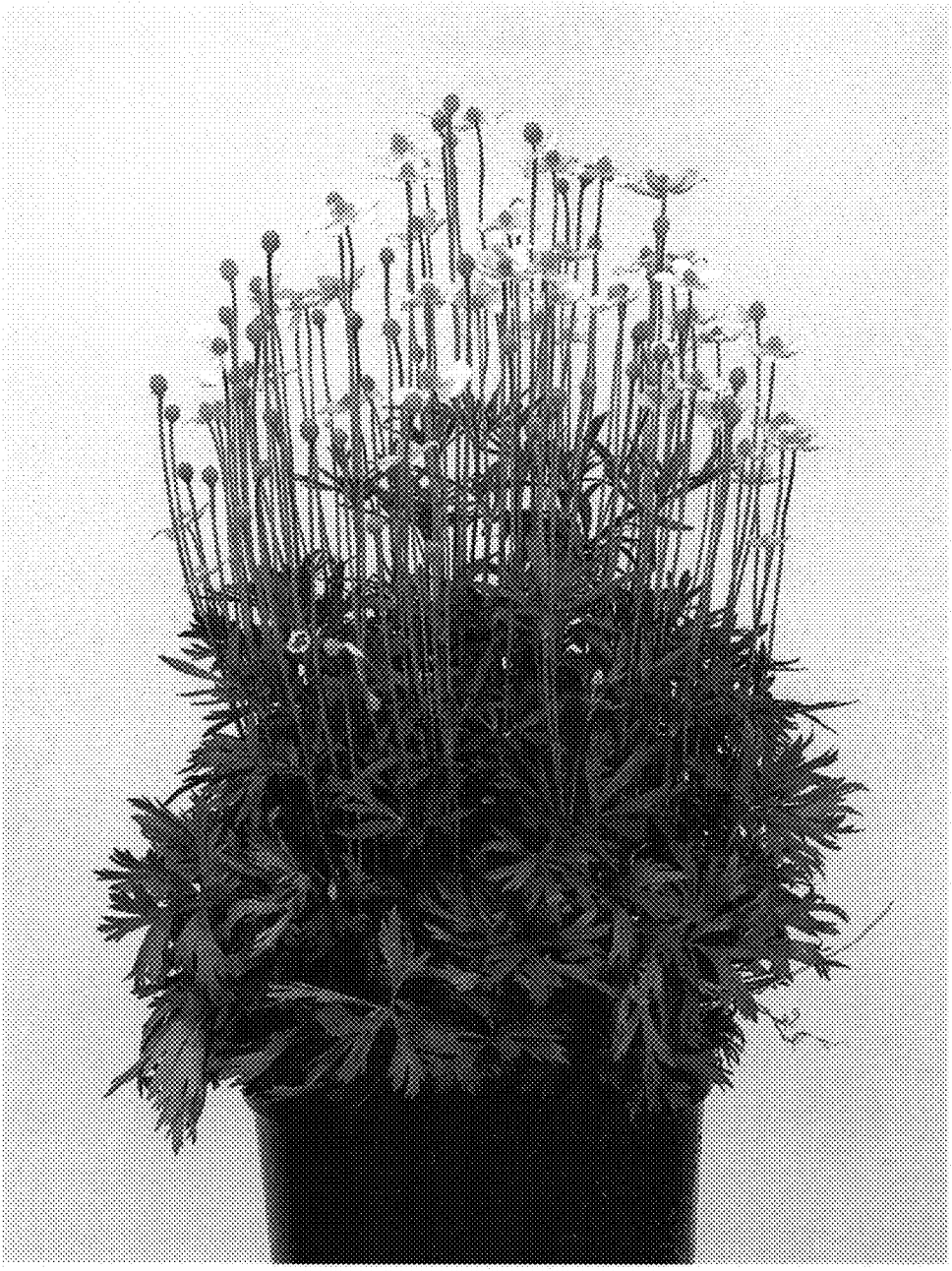

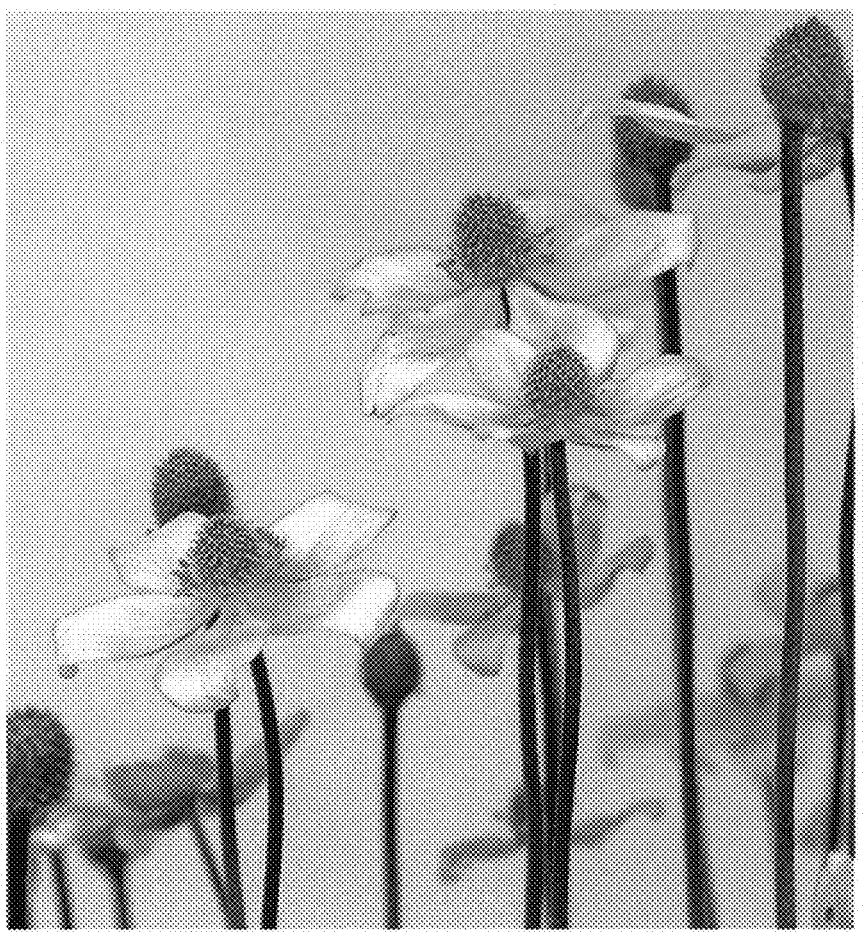
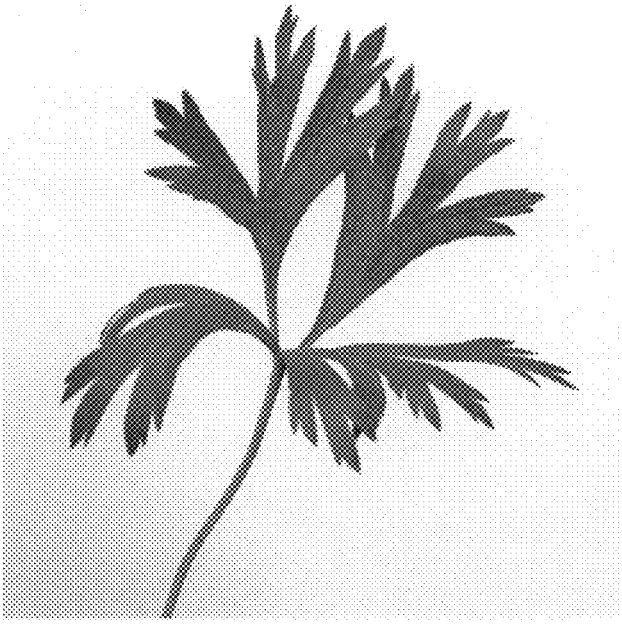

* * * * *